United States Patent
Hugues

(10) Patent No.: US 6,626,910 B1
(45) Date of Patent: Sep. 30, 2003

(54) DEVICE FOR ANCHORING A LIGAMENT TO AN OSSEOUS STRUCTURE FOR LIGAMENTOPLASTY

(76) Inventor: Charles Hugues, 10bis avenue Foch, 59420 Mouvaux (FR)

( * ) Notice: Subject to any disclaimer, the term of this patent is extended or adjusted under 35 U.S.C. 154(b) by 0 days.

(21) Appl. No.: 09/557,918

(22) Filed: Apr. 21, 2000

(30) Foreign Application Priority Data

Apr. 22, 1999 (FR) .............................. PCT/FR99/00955

(51) Int. Cl.[7] .............................................. A61B 17/56
(52) U.S. Cl. ..................................... 606/72; 606/151
(58) Field of Search ......................... 623/13.14, 13.11; 606/72, 151, 155, 60, 53, 232

(56) References Cited

U.S. PATENT DOCUMENTS

| | | | |
|---|---|---|---|
| 5,030,224 A | * 7/1991 | Wright et al. | 600/209 |
| 5,372,604 A | * 12/1994 | Trott | 411/922 |
| 5,501,696 A | * 3/1996 | Trott | 24/546 |

FOREIGN PATENT DOCUMENTS

| | | |
|---|---|---|
| FR | 2.721.818 | 1/1996 |
| FR | 2.731.610 | 9/1996 |
| FR | 2.737.104 | 1/1997 |

* cited by examiner

*Primary Examiner*—Kevin Shaver
*Assistant Examiner*—Melba Bumgarner
(74) *Attorney, Agent, or Firm*—Miles & Stockbridge P.C.; Edward J. Kondracki

(57) ABSTRACT

The invention relates to a device for anchoring a ligament to an osseous structure comprising a slender body (4) wherein one end (5) has a means (6) for fastening to the osseous structure and wherein the other end (7) has a loop (8) for at least indirectly attaching the ligament to it.

This device is characterized in that the fastening means (6) comprises at least two hooks (9) extending in divergent directions and secant to the longitudinal axis (10) of the body (4) of the device, and each hook (9) is carried by the end of a slender branch, and the slender branches constituting the body of the device progressively diverge from one another beginning at the loop (8) with which they are associated.

6 Claims, 2 Drawing Sheets

DEVICE FOR ANCHORING A LIGAMENT TO AN OSSEOUS STRUCTURE FOR LIGAMENTOPLASTY

FIELD OF THE INVENTION

The invention relates to a device for anchoring a ligament to an osseous structure for ligamentoplasty

BACKGROUND OF THE INVENTION

Occasionally there is a rupture of the connection between the end of a ligament and the bone to which it was initially attached.

Since the ligament cannot be reattached naturally, anchoring devices are used to fasten to the osseous structure, and to which the ligament is attached.

An anchoring device of this type conventionally comprises a slender body, wherein one end has a means for fastening to an osseous structure and wherein the other end has a loop for at least indirectly attaching the ligament to it.

There is, for example, a known anchoring device FR-A-2.731.610 forming a harpoon comprising a revolving cylindrical body, cut into the periphery of which are fins whose free ends extend progressively outward from the aforementioned body in order to anchor into the osseous structure.

As traction is exerted on the head of the anchoring device, the free ends of these fins penetrate into the osseous structure.

The head of this device is provided with a recess for at least indirectly attaching the ligament.

This device is inserted by force into a hole drilled into the bone, so that the fins projecting outward from the longitudinal axis prevent any retraction of the device by penetrating into the wall of the hole.

The tensile strength of these anchoring devices is nevertheless relatively weak.

In a different medical field that involves the reduction of fractures, there is a known device (FR-A-2.721.818 or FR-A-2.737.104) having the shape of a grapple, ie., having as fastening means two branches bent back 180° (one hundred eighty degrees) relative to the longitudinal axis of the body, and whose free ends are sharp in order to penetrate into the bone, and particularly into the cortical bone.

Once in place, these devices are wedged so as to exert a traction on the two parts of the bone, bringing the two parts closer together.

These devices cannot be used in any way in ligamentoplasty.

One of the objects of the invention is to obtain a device for ligamentoplasty that specifically eliminates the above-mentioned drawbacks.

SUMMARY OF THE INVENTION

To this end the subject of the invention is an anchoring device of the above-mentioned type comprising a slender body, wherein one end has a means for fastening to an osseous structure and wherein the other end has a loop for at least indirectly attaching the ligament to it, this device being characterized in that the fastening means comprises at least two hooks extending in divergent directions and secant to the longitudinal axis of the body of the device, and each book is carried by the end of a slender branch, and the slender branches constituting the body of the device progressively diverge from one another beginning at the loop with which they are associated.

DESCRIPTION OF THE DRAWINGS

The invention will be more clearly understood with the aid of the following description, given as a non-limiting example in reference to the attached drawing, which schematically represents.

DETAILED DESCRIPTION

Figure 1:
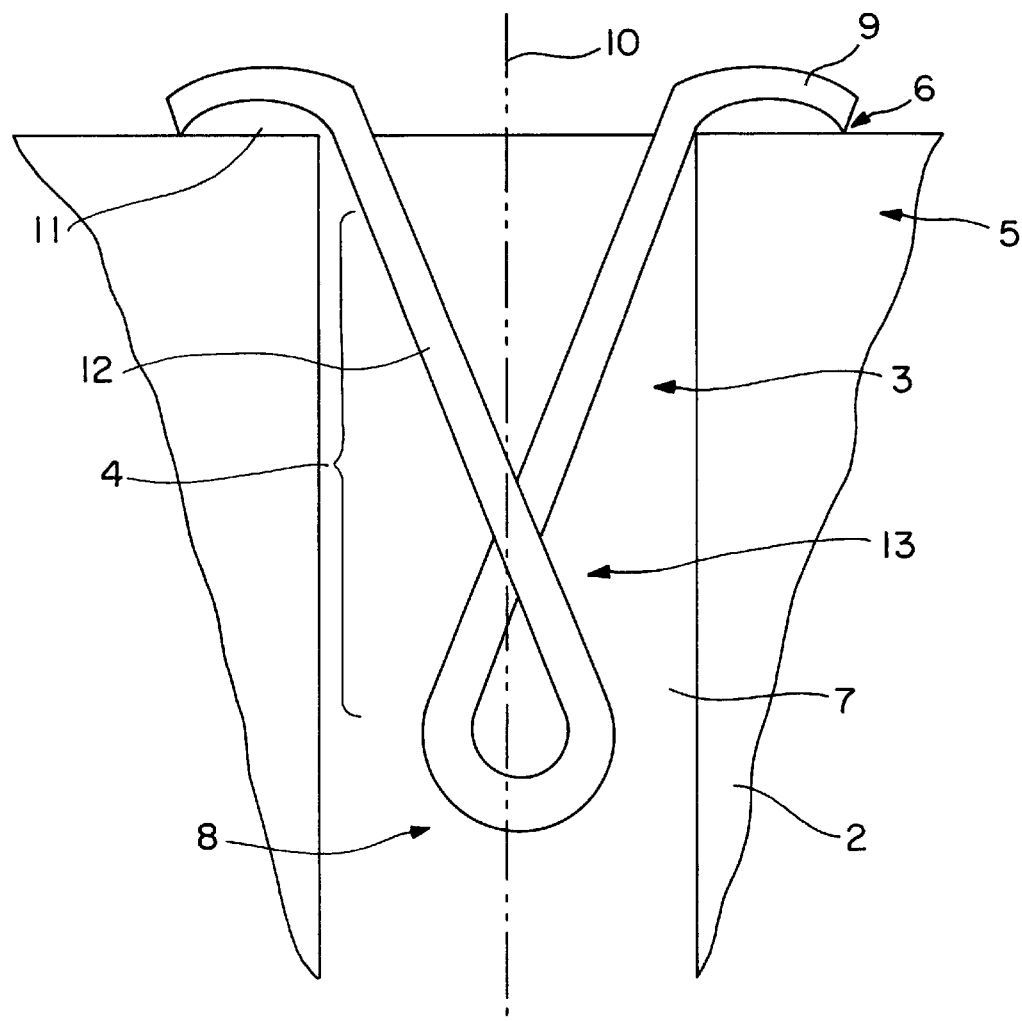
FIG. 1: an anchoring device according to the present invention.

Referring to the drawings, it may be seen that in order to attach a ligament 1 to an osseous structure 2, as in the attachment of a ligament to the shoulder or the knee, the anchoring device 3 according to the present invention comprises a slender body 4 wherein one end 5 has a means 6 for fastening to the osseous structure and wherein the other end 7 has a loop 8 for at least indirectly attaching the ligament to it.

The fastening means 6 comprises at least two hooks 9 extending in divergent directions and secant to the longitudinal axis 10 of the body 4 of the device.

Each hook 9 is carried by the end of a slender branch 12, and the slender branches 12 constituting the body of the device progressively diverge from one another beginning at the loop 8 with which they are associated.

In one embodiment, the body of the device is not elastically deformable, at least in the plane defined by the two branches.

According to another embodiment, the branches 12 of the body comprise an elastic means 13 for making it possible to momentarily bring the ends carrying the hooks closer together and to place the entire device into a cylindrical volume of reduced cross-section in order to insert the device through the skin and/or through a bore created in the head of the bone.

The body is thus at least locally elastic.

The hooks 9 each have a bearing surface 11 facing the loop 8 for resting against the external surface of the osseous structure, also known as the cortical bone.

These hooks are slightly curved and their ends are not sharp, so that the free ends of the hooks almost do not penetrate into the cortical bone.

By simply resting against the cortical bone, which is the strongest part of the bone, and by having a bearing surface that is relatively large as compared to the existing devices, much greater tensile strength is obtained than can be achieved with existing devices.

These bearing surfaces of hooks 9 are of circular, and possibly prismatic, cross-section.

In the elastic body embodiment, the device will be supplied to surgeons in a sheath in the closed position, and will open out the moment it is used.

The device 3 is composed of two branches 12 that cross to form the loop to which the ligament is indirectly attached.

This technical characteristic of the loop formed by crossing the branches makes the product extremely easy to use when it comes to threading wire through the hole of the loop by sliding the cord between the branches.

This formation of an open loop by crossing the branches distributes the mechanical stresses which, in a U-shaped attachment, would essentially be localized at the level of each fold or junction between a vertical branch and a horizontal branch.

For example, to attach the rotator cuff, the surgeon uses an ancillary element 14 comprising a curved trocar 15 by means of which it passes through the osseous structure.

Figure 3:
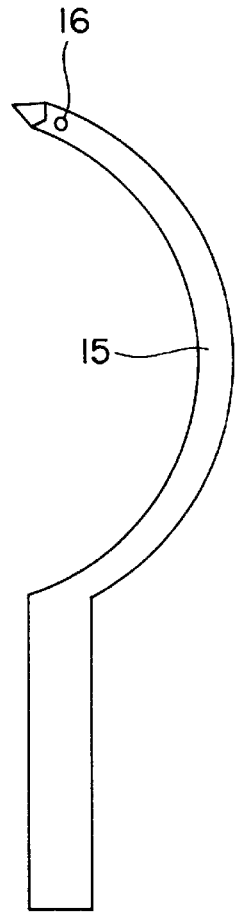

As shown in FIG. 3, the point of this curved trocar has a hole 16 through which wires may be temporarily threaded to be subsequently attached to the loop of the device and to the ligaments to be reattached.

Figure 2:
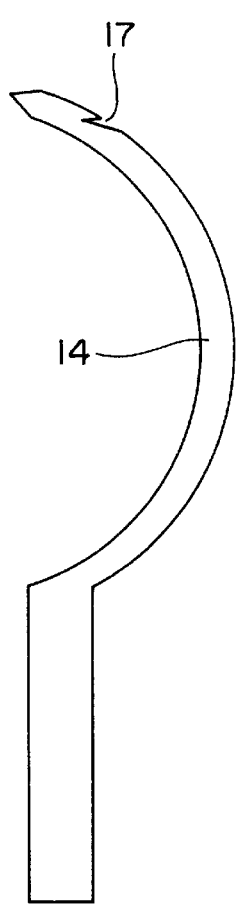
FIGS. 2 through 4: various ancillary elements for the insertion.
Figure 4:
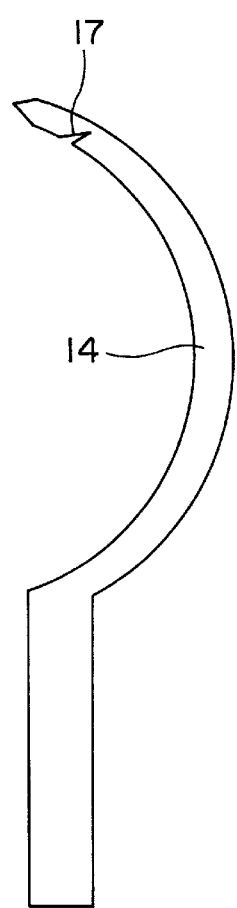

In a variant of embodiment, instead of a hole, a notch 17 is provided on the outside or the inside of the concavity of the curved trocar 15 as shown in FIGS. 2 and 4.

The device is inserted through the skin and placed in the required position, the device then resting, with its body housed in the passage created by the ancillary element and the hooks disposed on the outside, against the cortical bone.

In the event of a ligamentoplasty of the knee, after having drilled into the osseous structure a hole whose bottom comprises a canal of smaller cross-section, the device is pulled from outside to inside by a pull-through wire after a cutaneous incision.

It is then applied by simple traction to the external cortical bone.

The ligamentous transplant is passed through the eye of the implant ahead of time.

The wire is inserted with the aid of an eyed needle ahead of time.

The semitendinous and inner right tendons form loops passed through the loop of the anchoring device.

The bore is then filled with an osseous graft.

While this invention has been described in conjunction with specific embodiments thereof, it is evident that many alternatives, modifications and variations will be apparent to those skilled in the art. Accordingly, the preferred embodiments of the invention as set forth herein, are intended to be illustrative, not limiting. Various changes may be made without departing from the true spirit and full scope of the invention as set forth herein and defined in the claims.

What is claimed is:

1. A device for anchoring a ligament to an osseous structure, comprising:

a slender body having a first end which includes means at said first end for fastening the slender body to the osseous structure and a loop at a second end for at least indirectly fastening the ligament to the device;

the means for fastening the slender body to the osseous structure comprising at least two hooks extending in divergent directions and at a tangent to a longitudinal axis of the slender body;

the slender body comprising at least two slender branches that progressively diverge from one another beginning at the loop; and said at least two hooks being disposed at an end of said at least two slender branches, so as to rest against the osseous structure without penetrating the osseous structure.

2. A device for anchoring a ligament according to claim 1, wherein the at least two slender branches cross to form the loop.

3. A device for anchoring a ligament according to claim 1, wherein the body of the device is inflexible in the plane in which the at least two slender branches lie.

4. A device for anchoring a ligament according to claim 1, wherein the at least two slender branches of the slender body form an elastic means for momentarily bringing the at least two hooks on the ends of the at least two slender branches closer together so that the entire device can be placed into a cylindrical volume of reduced cross-section and inserted through skin for/or through a bore created in the osseous structure.

5. A device for anchoring a ligament according to claim 1, wherein the at least two hooks have blunt bearing surfaces facing the loop and resting against an external surface of the osseous structure.

6. A device for anchoring a ligament according to claim 5, wherein the bearing surfaces have a circular cross section.

\* \* \* \* \*